US008312877B2

(12) United States Patent
Elaz et al.

(10) Patent No.: US 8,312,877 B2
(45) Date of Patent: Nov. 20, 2012

(54) MODULAR MEDICAL CARE SYSTEM (75) Inventors: Joseph Elaz, North Andover, MA (US); Clifford Mark Kelly, Wells, ME (US); Wolfgang Scholz, Beverly, MA (US); Samuel Cavallaro, Warner, NH (US); Thomas Krüger, Reinfeld (DE); Martin Doering, Stapelfeld (DE); Christoph Landowski, Stockelsdorf (DE)

(73) Assignee: Draeger Medical Systems, Inc., Andover, MA (US)

( * ) Notice: Subject to any disclaimer, the term of this patent is extended or adjusted under 35 U.S.C. 154(b) by 1192 days.

(21) Appl. No.: 11/961,071

(22) Filed: Dec. 20, 2007

(65) Prior Publication Data

US 2008/0110460 A1    May 15, 2008

Related U.S. Application Data (62) Division of application No. 10/974,983, filed on Oct. 27, 2004, now abandoned.

(60) Provisional application No. 60/519,177, filed on Nov. 12, 2003.

(51) Int. Cl.
*A61M 16/00* (2006.01)

(52) U.S. Cl. ......... 128/204.21; 128/200.24; 128/202.27; 128/203.12; 128/204.18; 128/204.23

(58) Field of Classification Search ............. 128/200.24, 128/204.18, 204.21, 203.12, 202.27
See application file for complete search history.

(56) References Cited

U.S. PATENT DOCUMENTS

| | | | |
|---|---|---|---|
| 3,762,398 A | 10/1973 | Schefke et al. | |
| 4,651,731 A | 3/1987 | Vicenzi et al. | |
| 4,756,706 A | 7/1988 | Kerns et al. | |
| 4,823,787 A | 4/1989 | Adahan | |
| 4,883,051 A * | 11/1989 | Westenskow et al. | ... 128/204.21 |
| 4,905,688 A | 3/1990 | Vicenzi et al. | |
| 5,024,225 A | 6/1991 | Fang | |
| 5,337,845 A | 8/1994 | Foster et al. | |
| 5,375,604 A | 12/1994 | Kelly et al. | |
| 5,398,676 A * | 3/1995 | Press et al. | ............... 128/204.23 |
| 5,452,180 A | 9/1995 | Register | |
| 5,590,648 A | 1/1997 | Mitchell et al. | |
| 5,664,270 A | 9/1997 | Bell et al. | |
| 5,685,314 A | 11/1997 | Geheb et al. | |
| 5,687,717 A * | 11/1997 | Halpern et al. | ............... 600/300 |
| 5,701,894 A | 12/1997 | Cherry et al. | |
| 5,713,856 A | 2/1998 | Eggers et al. | |
| 5,752,917 A | 5/1998 | Fuchs | |
| 5,782,805 A | 7/1998 | Meinzer et al. | |
| 5,856,929 A | 1/1999 | McClendon et al. | |

(Continued)

FOREIGN PATENT DOCUMENTS

EP         0960627         12/1999

(Continued)

*Primary Examiner* — Clinton T Ostrup
(74) *Attorney, Agent, or Firm* — Mintz, Levin, Cohn, Ferris, Glovsky and Popeo P.C.

(57) ABSTRACT

A modular medical care system, housing a plurality of different modules providing different functions used in delivering healthcare to a patient, includes a plurality of different modules including: (a) a patient monitoring module for acquiring and processing signals derived from sensors suitable for attachment to a patient; and (b) a patient treatment module for delivering treatment to the patient. A processor processes signals derived from the plurality of different modules. A communication interface provides bidirectional communication between the processor and the plurality of different modules via a network.

14 Claims, 5 Drawing Sheets

U.S. PATENT DOCUMENTS

| | | |
|---|---|---|
| 5,961,448 A | 10/1999 | Swenson et al. |
| 6,055,981 A | 5/2000 | Laswick et al. |
| 6,083,156 A | 7/2000 | Lisiecki |
| 6,183,417 B1 | 2/2001 | Geheb et al. |
| 6,186,977 B1 | 2/2001 | Andrews et al. |
| 6,221,012 B1 | 4/2001 | Maschke et al. |
| 6,317,631 B1 | 11/2001 | Ben Haim et al. |
| 6,406,426 B1 | 6/2002 | Reuss et al. |
| 6,524,240 B1 | 2/2003 | Thede |
| 6,543,449 B1 * | 4/2003 | Woodring et al. ....... 128/204.18 |
| 6,544,174 B2 | 4/2003 | West et al. |
| 7,040,318 B2 * | 5/2006 | Dascher et al. .......... 128/204.21 |
| 7,080,646 B2 * | 7/2006 | Wiesmann et al. ...... 128/204.26 |
| 7,156,807 B2 | 1/2007 | Carter et al. |
| 7,188,621 B2 | 3/2007 | Devries et al. |
| 2002/0013518 A1 | 1/2002 | West et al. |
| 2002/0069877 A1 | 6/2002 | Villareal et al. |
| 2003/0052787 A1 | 3/2003 | Zerhusen et al. |
| 2003/0172931 A1 * | 9/2003 | Kerechanin et al. ..... 128/204.21 |
| 2004/0200477 A1 | 10/2004 | Bleys et al. |
| 2005/0056283 A1 | 3/2005 | Levi et al. |
| 2006/0249155 A1 | 11/2006 | Gambone |

FOREIGN PATENT DOCUMENTS

| | | |
|---|---|---|
| EP | 1085446 A2 * | 3/2001 |
| EP | 0796590 B1 | 6/2003 |
| WO | WO97/06843 | 2/1997 |
| WO | WO 02078775 A2 * | 10/2002 |
| WO | WO03/053503 | 7/2003 |

* cited by examiner

MODULAR MEDICAL CARE SYSTEM

CROSS-REFERENCED TO RELATED APPLICATIONS

This application is a divisional application of U.S. Non-Provisional application Ser. No. 10/974,983 Filed Oct. 27, 2004, now abandoned, which claims priority benefit under 35 U.S.C. 119 (e) of U.S. provisional application Ser. No. 60/519,177, filed Nov. 12, 2003. The filing dates and disclosures of the patent applications are hereby incorporated herein by reference in their entireties.

BACKGROUND OF THE INVENTION

Hospitals routinely monitor physiological parameters of patients from first entry until final release. Originally, this was performed by one or more patient monitoring devices, such as a heart rate monitor, an EKG monitor, an $SpO_2$ monitor, and so forth. These physiological parameters were separately detected by separate pieces of equipment, possibly manufactured by respectively different manufacturers. The monitoring equipment included the connections to the patient necessary to measure the physiological parameter and a display device of the type necessary to display the physiological parameter in an appropriate manner. A healthcare worker, such as a nurse, visited the patient's location and looked at each separate system to accumulate the patient's vital signs.

Current systems have integrated measurement of some of the physiological parameters (e.g. EKG, $SpO_2$, etc.) into a single patient monitoring device. Such a device includes the patient connections necessary to measure the physiological parameters measurable by the device and a display device which can display the measured physiological parameters in an appropriate manner. Such patient monitors may be considered to be partitioned into two sections. A first, operational, section controls the reception of signals from the electrodes connected to the patient and performs the signal processing necessary to calculate the desired physiological parameters. A second, control, status and communication, section interacts with a user to receive control information and with the operational section to receive the physiological parameters, and displays status information and the values of the physiological parameters in an appropriate manner. Either or both of these sections may include a computer or processor to control the operation of that section. This approach has an economic advantage since the control, status and communication section is shared among the parameter monitoring functions.

Such patient monitors may also be connected to a central hospital computer system via a hospital network. In this manner, data representing patient physiological parameters may be transferred to the central hospital computer system for temporary or permanent storage in a storage device. Data received from the patient monitors may also be monitored by a person, such as a nurse, at the central location. The stored data may be retrieved and analyzed by other healthcare workers via the hospital network. Patient monitors in such a networked system include a terminal which is capable of being connected to and communicating with the hospital network. In such a patient monitor, the control, status and communication section controls, not only the display of the physiological parameters, but also the connection to the hospital network and the exchange of the physiological parameters with other systems, such as other patient monitors and/or the central computer storage device, via the hospital network.

Such patient monitoring modules may also be portable. That is, they may operate while being transported with a patient who is being moved from one location to another in the hospital, for example, between a patient room and a therapy or operating room. A portable patient monitor consists of a base unit, and a portable unit which may be docked and undocked from the base unit. Base units may be placed at appropriate locations in the hospital. They are permanently connected to the hospital network and receive power from the power mains. The portable unit includes the necessary patient connections, connections for docking with base units, and a display screen. The portable unit also includes a processor which controls the operation of the portable unit The portable unit further includes a battery and an internal memory device.

While the portable unit of the patient monitor is docked, the batteries are recharged, and data representing physiological parameters are transmitted to the central hospital computer through the base unit via the hospital network. While the portable unit of the patient monitor is undocked, it runs on battery power. During transportation, the patient monitor continues to receive and display physiological parameters, and stores a record of those parameters in the internal memory device. If a base unit is available at the destination, the portable unit may be docked there. Communications is reestablished with the hospital central computer, and battery recharging commenced. At this time, data representing the previously stored parameters is retrieved from the internal memory device and transmitted to the storage device in the central hospital computer via the hospital network.

In such a patient monitor, the control, status and communication section controls, not only display of the physiological parameters, and communication of those parameters to the hospital network via the docking unit, but also detection of docking and undocking, control of power (either from the base unit when docked or the internal battery when undocked), storage of physiological parameter data in internal memory when the patient monitor is undocked, and transmission of stored physiological parameter data when the patient monitor is redocked.

Patient monitors have also been adapted to be used to transmit information to the hospital network from other modules. These modules may be patient monitoring modules measuring physiological parameters which are not measured by the patient monitor, or patient treatment modules reporting the status of treatments being provided to the patient. Such patient monitors include input terminals, or wireless input ports, to which these other monitoring modules are connected. Information from these modules is passed through the patient monitor to the hospital network through the base unit.

Figure 1:
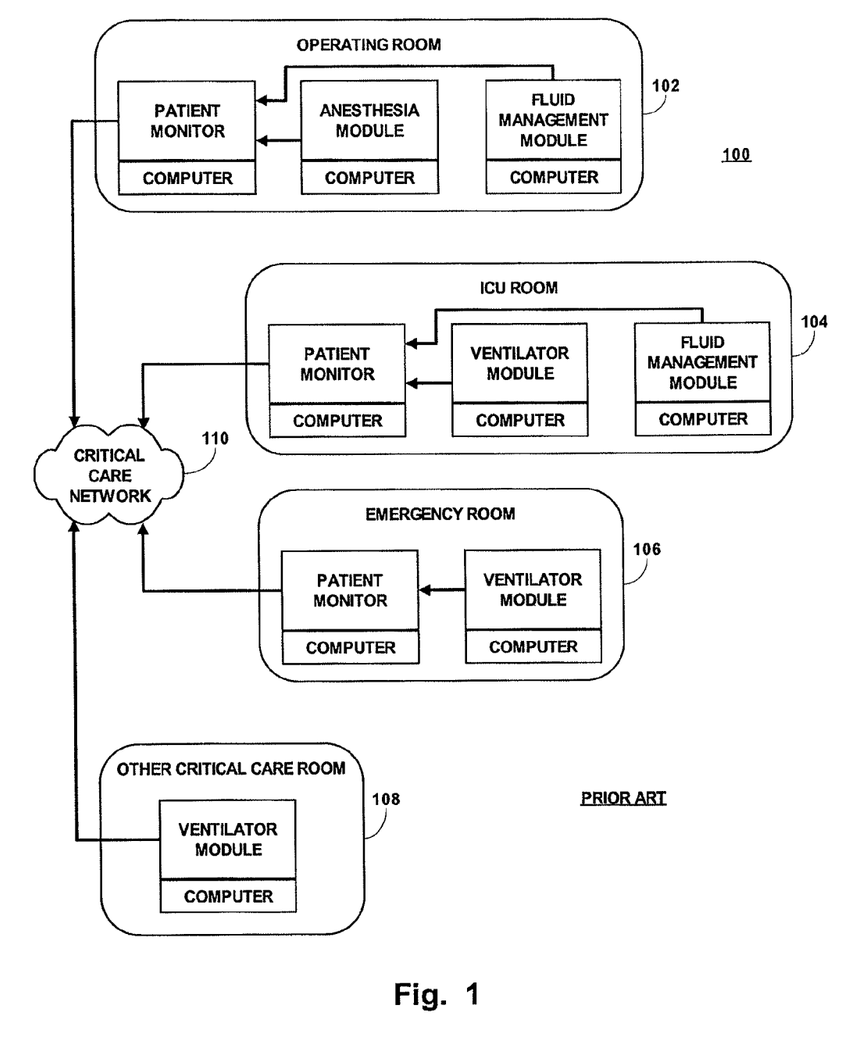
FIG. 1 is a block diagram of a prior art hospital system for monitoring patients and providing treatment to patients.

FIG. 1 is a block diagram of a hospital 100 operating in the manner described above. In FIG. 1, four rooms in a hospital are illustrated: an operating room 102, an intensive care unit (ICU) room 104, an emergency room 106 and another critical care room 108. The operating room 102, the ICU room 104 and the emergency room 106 include a patient monitor device as described above. Each patient monitor includes a connection to a critical care area network 110, either directly from the patient monitor or through a base unit (not shown). Each patient monitor also includes patient connections to electrodes attachable to the patient, not shown to simplify the figure. The patient monitors also receive data from other devices and forward that data to the critical care area network. In the operating room 102, an anesthesia device and fluid management device are coupled to the critical care area network 110 through the patient monitor; in the ICU room a ventilator device and fluid management device are coupled to the critical care area network 110 through the patient monitor;

and in the emergency room 106 a ventilator device is coupled to the critical care area network 110 through the patient monitor. In the other critical care room 108 a ventilator device is coupled directly to the critical care area network 110, either directly or through its own base unit.

A patient monitor is passive in the sense that it monitors physiological parameters of the patient to which it is attached. However, other medical devices are active in the sense that their operation affects the patient in some manner. For example, the anesthesia device controls the administration of anesthesia to a patient, e.g. during an operation; the fluid management device controls the administration of fluids (blood, saline, and/or medication) to a patient; the ventilator device assists or controls breathing of a patient, e.g. during an operation, and so forth. The active devices also include a computer or processor which controls the operation of the device. These devices also may be connected to a hospital network through a base unit. This allows a central location to not only monitor but also to control the active device. As with the patient monitoring device, an active device, such as a fluid monitoring device, may be portable in the sense that a control module, including a processor, may be undocked from a fixed unit. This control module continues to operate the device, at the last received control settings, e.g. while a patient is transported from one location to another. When at the new location, the control module may be docked in a fixed unit at the new location and control by a central computer resumed.

The modules illustrated in FIG. 1 operate independently of each other, and each includes its own computer or processor controlling the module. This requires the presence of a base unit for each separate module. In an operating room, where many such modules may be in use concurrently, this requires space, and power. Further, each device may be docked only in a base unit for that type of device. That is, a patient monitor device may be docked only in a patient monitor base unit, a fluid monitoring device may be docked only in a fluid monitoring device base unit, and so forth.

Furthermore, each module has its own user interface which may be different from those of other modules. This complicates the job of a healthcare provider by requiring training in the operation of the different modules. It also requires that, in order to provide a desired therapy, different modules from different manufactures be assembled around the patient, hooked up to the patient, control parameters set and continued operation monitored, with the difficulty, described above, related to different user interfaces of the different modules. Separate instructions on how to operate the different modules in the proper order with the proper settings, often depending on readings from other modules, must be provided to the healthcare provider to enable the desired therapy to be provided to the patient.

A medical care system which will alleviate the problems described above is desired.

BRIEF SUMMARY OF THE INVENTION

In accordance with principles of the present invention, a modular medical care system, housing a plurality of different modules providing different functions used in delivering healthcare to a patient, includes a plurality of different modules including: (a) a patient monitoring module for acquiring and processing signals derived from sensors suitable for attachment to a patient; and (b) a patient treatment module for delivering treatment to the patient. A processor processes signals derived from the plurality of different modules. A communication interface provides bidirectional communication between the processor and the plurality of different modules via a network.

DETAILED DESCRIPTION OF THE INVENTION

Figure 2:
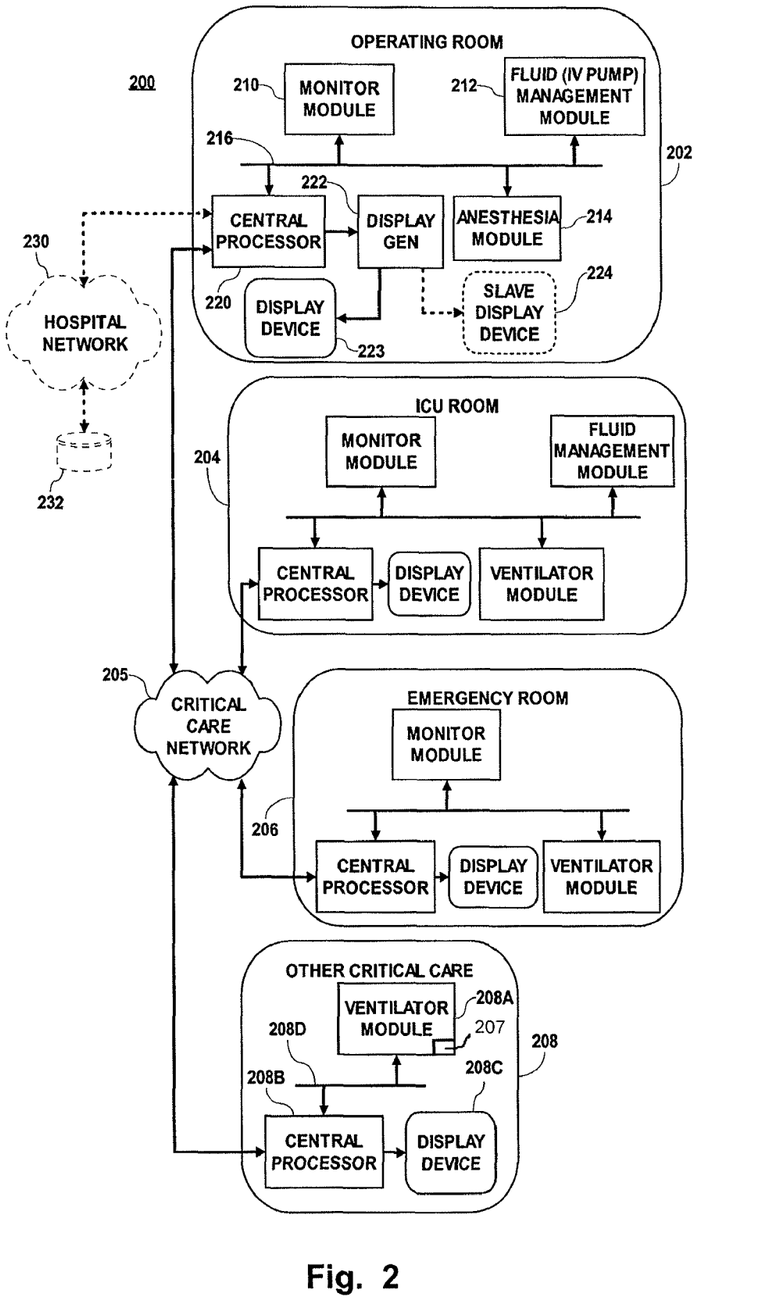
FIG. 2 is a block diagram of a hospital system for monitoring patients and providing treatment to patients according to principles of the present invention.

FIG. 2 is a block diagram of a hospital system 200 for monitoring and providing treatment to patients. In FIG. 2, the same four rooms are illustrated as are illustrated in FIG. 1, and those rooms contain the same medical equipment. The operating room 202 includes a patient monitoring module 210 for acquiring and processing signals derived from sensors (not shown) suitable for attachment to a patient. The operating room 202 also includes patient treatment modules: a fluid infusion (IV pump) control and management module 212 and an anesthesia module 214. These modules (210, 212 and 214) are coupled to a central processor 220 via a patient area network (PAN) 216. The central processor 220 is coupled to a display generator 222 which is coupled to a display device 223. The display generator 222 is also optionally coupled to a slave display device 224, as illustrated in phantom. The ICU room 204 includes a monitor module, a fluid management patient treatment module and a ventilator module, coupled to a central processor via a PAN. The emergency room 206 includes a monitor module and a ventilator patient treatment module coupled to a central processor via a PAN. The other critical care room 208 includes a ventilator patient treatment module coupled to the central computer via a PAN 216.

In operation, the PAN 216 may be implemented in any manner allowing a plurality of modules to intercommunicate. For example, the PAN 216 may be implemented as an Ethernet network, either wired or wireless (WLAN). If implemented as a wireless network, it may be implemented according to available standards, such as: (a) a WLAN 802.11b compatible standard, (b) 802.11a compatible standard, (c) 802.11g compatible standard, (d) Bluetooth 802.15 compatible standard, and/or (e) GSM/GPRS compatible standard communication network.

The patient monitoring module 210 corresponds to the operational portion of a prior art patient monitor described above. It receives signals from the electrodes and sensors attached to the patient, performs the signal processing required to calculate the physiological parameters, and provides that information to the central processor 220 via the PAN 216. Similarly, the patient treatment modules, i.e. the fluid management module 212 and the anesthesia module 214, correspond to the operational portion of the prior art treatment modules described above. The patient treatment modules 212, 214 receive operational data from the central processor 220 via the PAN 216 and in response perform their treatment functions, e.g. monitoring fluids administered to the patient and supplying anesthesia to the patient, respectively. Concurrently, the patient treatment modules 212, 214 send status data to the central processor 220 via the PAN 216. The central processor 220 processes the signals received from the patient monitoring module 210 and the patient treatment modules 212 and 214.

The central processor 220 interacts with the user to receive patient identifier information and treatment instructions and parameters. The central processor 220 configures the patient treatment modules 212, 214 by sending patient identifier information, the treatment instructions and parameters to the patient treatment modules 212 and 214 via the PAN 216.

The patient monitoring and/or treatment modules 210, 212, 214 may include a processor for receiving the configuration parameters from the central processor 220, for controlling the operation of the module 210, 212, 214 and for sending status and patient physiological parameter information to the central processor 220 via the PAN 216. The configuration parameters may include patient identifier information, set-up parameters, and/or data representing executable instructions for execution by the processor in the module 210, 212, 214 in processing data to be provided to the central processor 220. The modules 210, 212, 214, in turn, use the received configuration parameters, and executable instructions in supporting their operation, e.g. for processing data to be provided to the central processor 220.

As described above, there may be more than one central processor 220 in remote locations in the hospital. If a module 210, 212, 214 is disconnected from one central processor 220, then the patient identifier information, the set-up parameters and/or the executable instructions previously sent to it are used to control the operation of that module 210, 212, 214 while it is disconnected. If the disconnected module 210, 212, 214 is reconnected to a central processor 220, possibly in a different location than the central processor 220 from which it is disconnected, then the reconnected module 210, 212, 214 sends data representing the patient identifier information, the operational characteristics of the module, and any patient physiological parameter data gathered while disconnected to the central processor 220 to which it is connected.

The central processor 220 also receives signals representing physiological parameters from the patient monitoring module 210 and possibly from the patient treatment modules 212, 214. These parameters may be relatively standard physiological parameter, such as EKG, heart rate, SpO$_2$, etc. The central processor 220 may also initiate generation of a new parameter based on signals derived using the patient monitoring module 210 and/or the patient treatment modules 212, 214. For example, the new parameter may be associated with (a) gas exchange, (b) skin color, (c) haemodynamics, (d) pain and/or (e) electro-physiology.

The central processor 220 conditions the display generator 222 to generate signals representing an image for displaying these physiological parameters in an appropriate manner, e.g. a waveform, a status phrase or a number. The display generator 222 is coupled to the display device 223 which displays this image. The display generator 222 may optionally send appropriate image representative signals to the slave display device 224. The slave display device 224 may have a larger, higher resolution screen, or may simply be a display device at a location remote from the location of the central processor. The image generated by the display device 223, under the control of the central processor 220 and display generator 222, may also integrate the display of patient identification, treatment instructions and parameters and status from the patient treatment modules 212, 214 in an appropriate manner.

In this manner, information from users as well as patient monitoring modules 210 and patient treatment modules 212, 214 may be integrated into one or more composite images displayed on display devices 223 and 224, for example.

The central processor 220 may also communicate with the central processors of corresponding processing device and display systems in other locations in the hospital, such as those in the ICU room 204, the emergency room 206 and the other critical care room 208 via the critical care area network 205. The central processor 220 may optionally communicate with a central hospital location via a hospital network 230, illustrated in phantom in FIG. 2. In this manner, patient physiological parameters and treatment instructions, parameters and status may be transmitted to a central location and stored in a central storage device 232, also illustrated in phantom.

FIG. 2 illustrates a patient monitoring module 210, and patient treatment modules for fluid management 212, anesthesia control 214, and ventilation control. However, one skilled in the art will understand that there are other monitoring and treatment devices which may include patient treatment modules for control and communication, such as: (a) an incubator, (b) a defibrillator, (c) a warming module, (d) a diagnostic imaging module, (e) a photo-therapy module, (f) a fluid input support module, (g) a fluid output support module, (h) a heart—lung support module, (i) a blood gas monitor, (j) a controllable implanted therapy module, (k) a controllable surgical table and weighing scale, and so forth. Modules for command and communication related to these and other patient treatment devices may be used as illustrated in FIG. 2.

Figure 3:
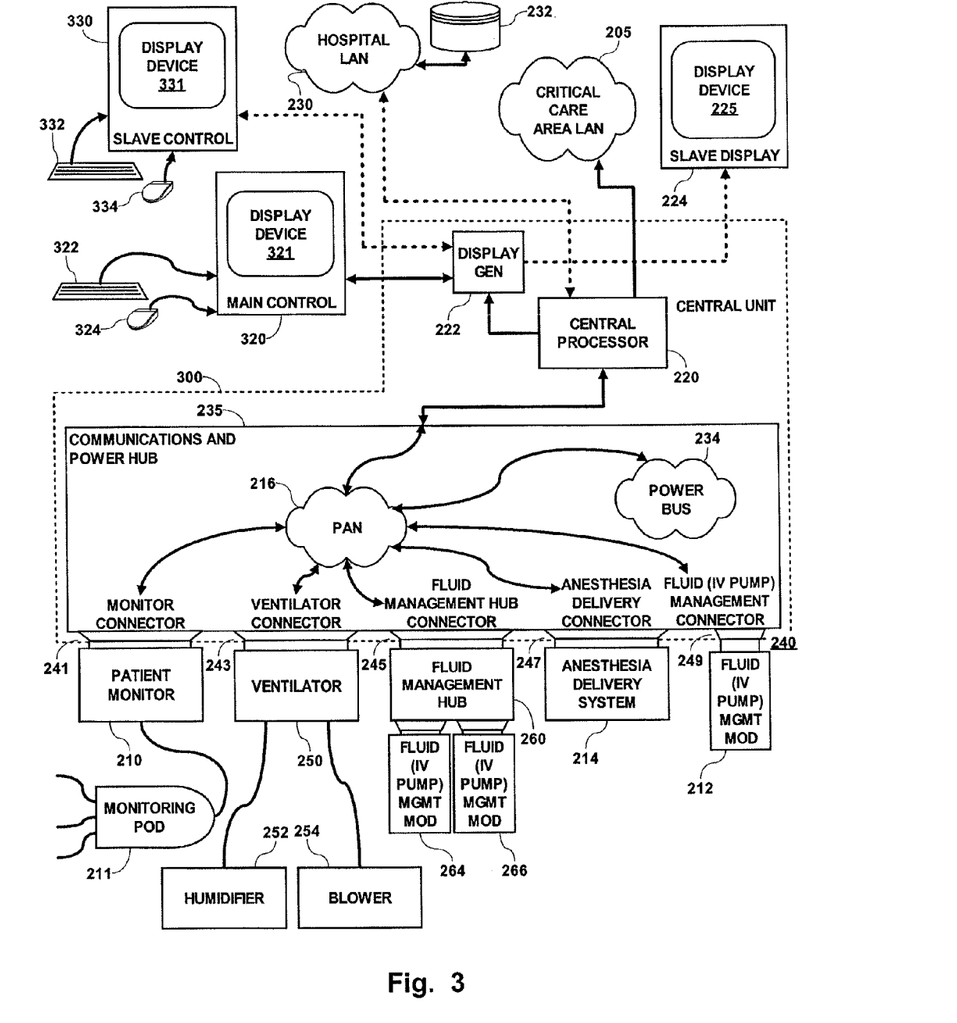
FIG. 3 is a more detailed block diagram illustrating the interconnections of the central processor and the patient monitoring and treatment modules.

FIG. 3 is a more detailed block diagram illustrating the system illustrated in FIG. 2. In FIG. 3, those elements which are the same as illustrated in FIG. 2 are designated by the same reference number and are not discussed in detail below. FIG. 3 illustrates the system as it would be implemented in one of the rooms 202, 204, 206 or 208 of FIG. 2. In FIG. 3, the central processor 220 and the display generator 222 are comprised within a central unit 300. The central unit 300 is a housing containing the circuitry and connectors necessary to interconnect the central processor 220 and the display generator 222 with: the patient monitoring and patient treatment modules 210, 212, 214, 250 and 260; the display devices 224, 320 and 330; and the multi-patient LAN 205 and hospital LAN 230.

The central processor 220 is coupled to a communications and power hub 235. The communications and power hub 235 comprises the patient area network (PAN) 216 and also a set 240 of module connectors coupled to the PAN 216: e.g. a patient monitor connector 241, a ventilator connector 243, a fluid management hub connector 245, an anesthesia delivery system connector 247 and a fluid (IV pump) management connector 249. The connectors 240 permit the individual modules 210, 212, 214, 250, 260 to be plugged into and removed from the central unit 300 as required. In one embodiment, a user may activate a single mechanical release mechanism to remove a module 210, 212, 214, 250, 260 from the central unit 300 or reattach a module to the central unit 300. The connectors 240 pass data signals between the modules 210, 212, 214, 250, 260 and the central processor 220 via the PAN 216.

The communications and power hub 235 further comprises a power bus 234 for distributing power to the central unit 300. The power bus 234 is further coupled to the PAN 216 for receiving commands from and returning status to the central processor 220. The power bus 234 is also coupled to the connectors 240 (not shown to simplify the figure) to distribute power to the patient monitoring and/or treatment modules 210, 212, 214, 250, 260. In this manner, the central processor 220 may manage the power-on and power-off status of the patient monitoring and treatment modules 210, 212, 214, 250, 260 in accordance with a set of predetermined rules maintained in the central processor 220.

As described above, at least some of the attached modules 210, 212, 214, 250, 260 include circuitry, e.g. batteries 207, which permit them to continue to operate when disconnected from the central unit 300. When docked, the central processor 220 conditions these modules 210, 212, 214, 250, 260 to transition from operating on battery power to operating on the power supplied by the power bus 234 and recharge their batteries 207. The internal power supply circuitry of these modules 210, 212, 214, 250, 260 may also supply power supply status information, e.g. current battery capacity, to the central processor 220 through the connectors 240 and PAN 216. The central processor 220 may condition the display generator 222 to generate signals representing an image showing the battery charging condition of the patient monitoring and treatment modules 210, 212, 214, 250, 260 plugged into the central unit 300. This image may be displayed on the display devices 321, 331 and/or 225 in the main control panel 320, slave control panel 330 and/or remote display device 224, respectively.

As described above, the PAN 216 may be implemented as a wireless network. In such an embodiment, the central processor 220 may include a wireless communication interface to the PAN 216. Such an interface enables bidirectional communication with the patient monitoring and treatment modules 210, 212, 214, 250, 260 when they are disconnected from the central unit 300. This communications link enables the central processor 300 to maintain control of the patient monitoring and treatment modules 210, 212, 214, 250, 260 while they are disconnected from the central unit.

Individual patient monitoring and/or treatment modules 210, 212, 214, 250, 260 are coupled to corresponding ones of the connectors 240. For example, a patient monitor module 210 may be plugged into the monitor connector 241, a ventilator module 250 may be plugged into the ventilator connector 243, and so forth. The central unit 300 may include connectors 241, 243, 245, 247, 249 which are specific to the type of patient monitoring or treatment module, 210, 212, 214, 250, 260, expected to be plugged in. Alternatively, the modules 210, 212, 214, 250, 260 may be fabricated with the same type of connector and the connectors 240 may be the same type of matching connectors. In the former embodiment, a particular type of patient monitoring or treatment module 210, 212, 214, 250, 260 may be plugged into a connector 241, 243, 245, 247, 248 corresponding to that type of module. In the latter embodiment, any patient monitoring or treatment module 210, 212, 214, 250, 260 may be interchangeably plugged into any of the connectors 241, 243, 245, 247, 248.

As described above, the patient monitor module 210, plugged into the monitor connector 241, connects to a plurality of electrodes and sensors which may be placed on a patient. A monitoring pod 211 is used to connect the patient-connected electrodes to the patient monitor module 210. Similarly a ventilator module 250 may be plugged into the ventilator connector 243. The ventilator module 250, in turn, is coupled to a blower 254 and a humidifier 252. A fluid management hub 260 is plugged into the fluid management hub connector 245. Two fluid (IV pump) management modules 264 and 266 are plugged into the fluid management hub 267. Each fluid (IV pump) management module, 264, 266, is connected to an IV pump (not shown). An anesthesia delivery module is plugged into an anesthesia delivery connector 247. The anesthesia delivery module 214 is connected to a anesthesia delivery device (not shown). An individual IV pump 212 is coupled to an IV pump connector 249. Similar to the other IV pump modules 264 and 266, the fluid (IV pump) management module 212 is connected to an IV pump (not shown).

The central processor 220 is also coupled to the critical care area LAN 205, which, as illustrated in FIG. 2, is coupled to other central units 300 in processing device and display systems in other rooms. The central processor 220 may also be optionally coupled to a hospital LAN 230. The critical care LAN 205 requires real time bandwidth quality-of-service while the hospital LAN 230 requires standard office bandwidth quality-of-service. As described above, if connected to a hospital LAN 230, the central processor 220 may exchange data with a central storage device 232, or any other desired device (not shown) at a remote location in the hospital. Data may be sent from patient monitoring and/or treatment modules 210, 212, 214, 250, 260 to the central storage device 232 through the connectors 240 to the central processor 220 via the PAN 216 and from there to the central storage device 232 via the hospital LAN 230. In addition, control data may be sent in the other direction from the central location to a patient monitoring or treatment module 210, 212, 214, 250, 260.

It is further possible that a central processor 220 in a central unit 300 in a processing device and display system in one treatment room 202, 204, 206, 208 may communicate with a second central processor 220 in a central unit 300 in a processing device and display system in a different treatment room 202, 204, 206, 208 (FIG. 2) via the critical care area LAN 205 or the hospital LAN 230. In this manner, the central processor 220 in one treatment room may control the operation of the second central processor 220 in the second treatment room; may display patient related data received from the second central unit 300 in the different treatment room; and/or may send (a) a patient identifier identifying a particular patient and/or (b) medical information related to the particular patient to the second central processor 220 in the central unit 300 in the second treatment room 202, 204, 206, 208, which receives this information.

It is also possible for the central processor 220 to receive data from one or more of the patient monitoring and/or treatment modules 210, 212, 214, 250, 260, process that data and send control data to one or more of the patient treatment modules 212, 214, 250, 260 in response to the received data, in a manner to be described in more detail below.

The display generator 222 is coupled to a main control panel 320. The main control panel 320 includes a display device 321, a keyboard 322 and a pointing device in the form of a mouse 324. Other input/output devices (not shown) may be fabricated on the main control panel 320, such as: buttons, switches, dials, or touch screens; lights, LCDs, or LEDs; buzzers, bells or other sound making devices, etc. These input/output devices receive signals from and supply signals to the central processor 220, either through the display generator 222, or through separate signal paths, not shown to simplify the figure. The main control panel 320 may be fabricated as a part of the central unit 300, or may be fabricated as a separate unit. The display generator 222 is optionally coupled to a slave control panel 330, which substantially duplicates the functionality of the main control panel 320, but is located remote from the central unit 300. The display generator 222 is also optionally coupled to a slave display device 224. The slave display device 224 includes a display device 225, but does not include any of the other input/output devices included in the main control panel 320 and slave control panel 330.

In operation, the central unit 300 and main control panel 320 provide control and display functions for the patient monitoring and/or treatment modules 210, 212, 214, 250, 260 which are plugged into the common unit 300. A user may manipulate the input devices coupled to the main control panel 320, or slave control panel 330 if available, e.g. the keyboard 322, mouse 324 or other input devices described above. The resulting signals are received by the central processor 220. In response, the central processor 220 sends control signals via the PAN 216 to the patient monitoring or treatment modules 210, 212, 214, 250, 260 which are currently plugged into the central unit 300.

Concurrently, the central processor 220 receives data signals from the patient monitoring and/or treatment modules 210, 212, 214, 250, 260, as described above, and conditions the display generator 222 to produce a signal representing an image for displaying the data from the patient monitoring and/or treatment modules 210, 212, 214, 250, 260, in an appropriate manner. For example, if a patient monitor 210 having the capability of performing an EKG on a patient is plugged into the central unit 300, EKG lead data from the patient monitor 210 is supplied to the central processor 220 through the monitor connector 241 via the PAN 216. The central processor 220, in turn, conditions the display generator 222 to produce signals representing an image of the EKG lead signal waveforms. These image representative signals are supplied to the display device 321 in the main control panel 320, which displays the image of the waveforms of the EKG lead signals. An image representing the heart rate of the patient, derived from the EKG lead signals, may also be similarly displayed in numeric form. Images representing other physiological parameters measured by the patient monitor 210, e.g. blood pressure, temperature, $SpO_2$, etc. may also be displayed, in an appropriate form, on the display device 321 of the main control panel 320 in a similar manner. The image data may also be displayed on the display device 331 of the slave control panel 330 and on the display device 225 of the slave display 224, if they are available.

In a similar manner, images representing data received from the patient treatment modules, 212, 214, 250, 260, may be displayed on the display devices 321, 331, 225 in an appropriate form. Such data may represent, for example, present settings for the respective treatment modules, such as specified drip rates for IV pumps attached to fluid management modules 212, 264, 266. This data may be represented by images of appropriate form. Such data may also represent physiological parameters which may be measured by the patient treatment devices 212, 214, 250, 260. For example, respiration loops may be displayed in graphical form based on data received from the ventilator module 250, or drip rates for attached IV pumps may be displayed in numerical form based on data received from the fluid management hub 260.

A user may select which physiological parameters to display on the display device 321 and may arrange the location on the display device 321 of the images displaying the selected physiological parameters. In addition, the user may select different physiological parameters to display on the display device 321 in the main control panel 320 than on the display device 331 in the slave control panel 330 and/or on the display device 225 in the slave display 224. Further, the slave display device 224 may have a display device 225 which is larger and/or higher resolution than those in the main control panel 320 and the slave control panel 330, so that the images may be more easily seen, and/or may be displayed at an increased resolution.

The central processor 220 may also receive data from the power bus 234 via the PAN 216 representing the state of the power supplies in the patient monitoring and treatment modules 210, 212, 214, 250, 260. The central processor 220 may, for example, condition the display generator 222 to generate a signal representing an image representing the current charge condition of the respective batteries in the patient monitoring and treatment modules 210, 212, 214, 250, 260 plugged into the central unit 300, either separately or in composite, based on data received from the power bus 234. Further, the patient monitoring and/or treatment modules 210, 212, 214, 250, 260 may provide data to the central processor 220 indicating an error condition in the module. The central processor 220 may condition the display generator 222 to generate a signal representing an image showing the user the error condition of that module.

The central processor 220 may also produce signals for controlling the operation of the other output devices on the main and slave control panel 320, 330, described above. For example, the central processor 220 may analyze the physiological parameters derived from signals received from the patient monitoring and/or treatment modules 210, 212, 214, 250, 260 to determine if any limits have been exceeded. This may entail separately calculating and verifying each physiological parameter response determined from a patient monitoring and/or treatment module, and comparing it to a predetermined parameter range to determine if it exceeds a limit, or analyzing more than one physiological parameter to determine if a function of those physiological parameters exceeds a limit. If a limit has been exceeded, then the central processor 220 may condition the output devices on the main and slave control panel 320, 330 to provide an alarm. For example, the central processor 220 may generate a signal which activates a light, a buzzer, a bell and/or other such device on the main control panel 320, and/or the slave control panel 330, if available, to produce a visible or an audible alarm. The central computer 220 may also send a signal over the critical care area LAN 205 and/or the hospital LAN 230 indicating that a limit has been exceeded. A similar alarm may be generated at the remote location in response to the receipt of this signal.

Figure 4:
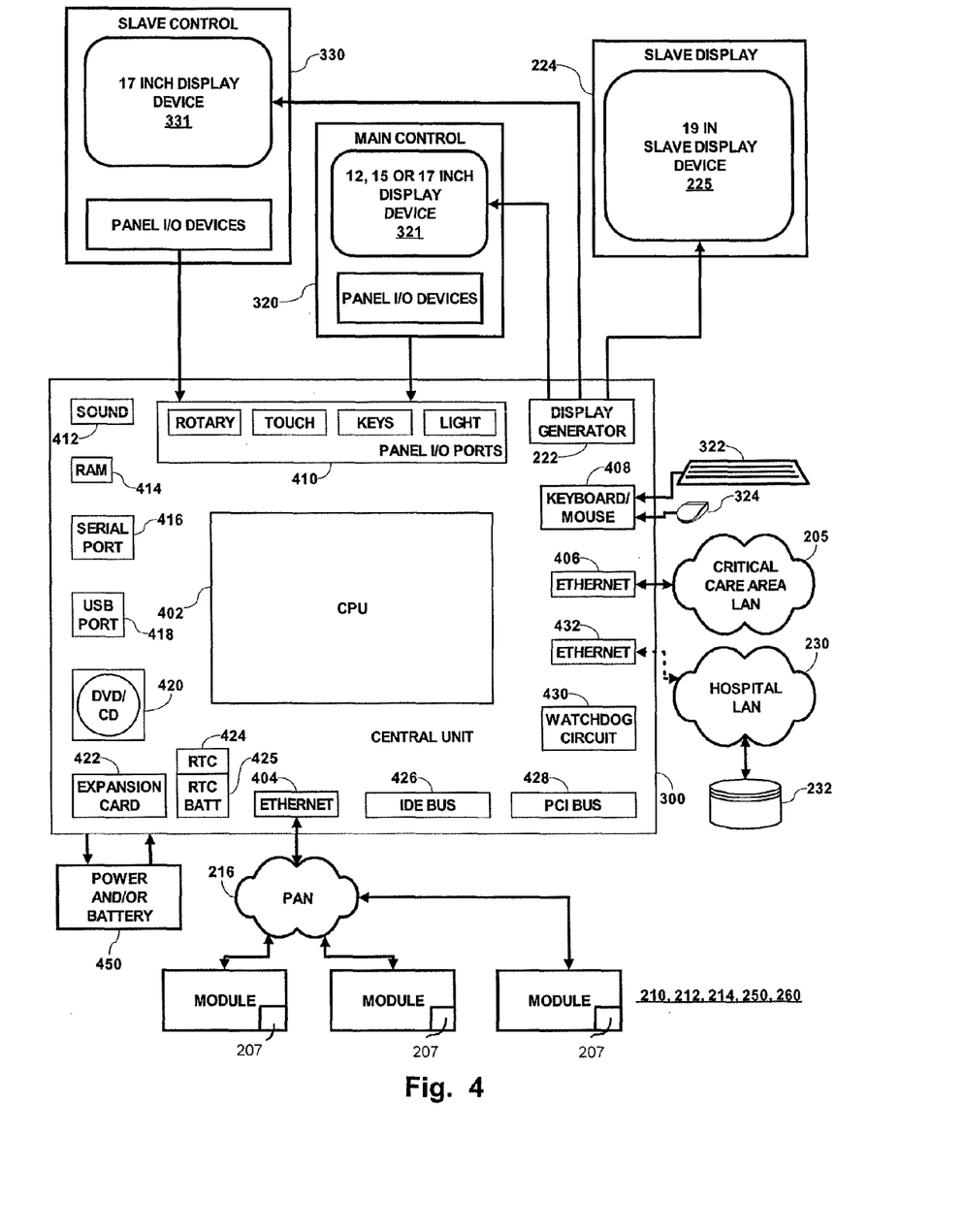
FIG. 4 is a more detailed block diagram of a central unit illustrated in FIG. 3.

FIG. 4 is a more detailed block diagram of a central unit 300 illustrated in FIG. 3. In FIG. 4, those elements which are the same as those illustrated in FIG. 3 are designated by the same reference numbers and are not described in detail below. In FIG. 4, the central unit 300 is implemented on a computer system similar to typical personal computers. In such systems, a central processing unit (CPU) 402 controls the operation of the remainder of the system. The other elements illustrated in the central unit 300 are coupled to the CPU 402, though the connections are not shown to simplify the figure.

In FIG. 4, a power supply 450 provides power to the central unit 300. The power supply 450 may be coupled to the power mains. The power supply 450 may also include batteries to provide power to the central unit 300. The batteries may operate in an emergency backup mode, in which if a power failure occurs at the power mains the battery is switched to supply power to the central unit. Alternatively, batteries may provide main power to the central unit, and the power mains used to maintain the battery at full charge, or to recharge the battery after a power failure. One skilled in the art will understand that other arrangements for supplying power to the central unit 300 are possible.

A first Ethernet adapter 404 couples the CPU 402 to the patient area network (PAN) 216, which in turn is interconnected with patient monitoring and/or treatment modules 210, 212, 214, 250, 260. A second Ethernet adapter 406 couples the CPU 402 to the critical care area LAN 205. A third Ethernet adapter 432 couples the CPU 402 to the hospital LAN 230 which in turn is interconnected with the central storage device 232.

The display generator 222 couples the CPU 402 to the display devices 321, 331 and 225 in the main control panel 320, the slave control panel 330 and the slave display 224, respectively. A set of panel I/O ports 410 couple the CPU 402 to the panel I/O devices, described above, on the main control panel 320 and the slave control panel 330. As previously described, such I/O devices may include rotary switches, touch panels, pushbutton keys, lights, and so forth.

A watchdog circuit 430 checks the proper operation of the CPU 402 and produces a signal indicating a fault condition if the CPU 402 is not operating properly. The watchdog circuit 430 may check for proper operation of the CPU 402 using any of a variety of methods. For example, the watchdog circuit 430 may send a challenge signal at regular intervals to the CPU 402. If the CPU 402 is operating properly, it receives and recognizes the challenge signal, and provides a reply signal back to the watchdog circuit 430. If the watchdog circuit 430 does not receive the reply signal back from the CPU 402 within a specified time of issuing the challenge signal, then it detects a fault in the CPU 402, and produces the fault condition signal. The watchdog circuit 430 may also attempt to restart operation, i.e. reboot of the CPU 402, upon detecting a fault in the operation of the CPU 402.

The remainder of the elements illustrated in the central unit 300 are typically included in personal computers. A keyboard/mouse interface 408, typically using a PS/2 or USB standard, couples the keyboard 332 and mouse 324 to the CPU 402. A sound card 412 responds to instructions from the CPU 402 to generate sound representative signals, which may be coupled to speakers (not shown) to reproduce sound. A read-write memory unit (RAM) 414 provides local storage for programs controlling the CPU 402 and for data used and/or created by the CPU 402. A serial port 416 exchanges serial binary data signals with external peripherals e.g. using the RS232 standard. A USB port 418 similarly exchanges serial binary data signals with external peripherals using the USB standard. A DVD/CD player 420 allows the CPU 402 to access data on DVDs and/or CDs. It is also possible to write data onto DVDs and/or CDs. An expansion card port 422 allows the CPU to exchange data with portable devices, such as a Personal Computer Memory Card International Association (PCMCIA) card, Compact Flash (CF), Secure Digital (SD), and so forth. A real time clock (RTC) 424 with its associated battery 425, maintains and provides current time and date to the CPU 402. An integrated drive electronics (IDE) bus 426, into which conforming cards may be plugged, allow such cards to exchange information with the CPU 402. Similarly, a peripheral component interconnect (PCI) bus, into which conforming cards may be plugged, allow such cards to exchange information with the CPU 402. Cards plugged into either the IDE bus 426 or the PCI bus 428 may be coupled to peripheral devices, both internal and external to the central unit 300, and permit the CPU 402 to exchange data with the peripheral devices.

In operation, the CPU 402 interacts with the peripheral devices connected to it under control of software. Because the central unit 300 is designed and implemented similarly to a typical personal computer, it may be controlled using software typically executed on a personal computer, augmented by executable applications for performing specialized tasks related to monitoring and providing treatment to patients.

Figure 5:
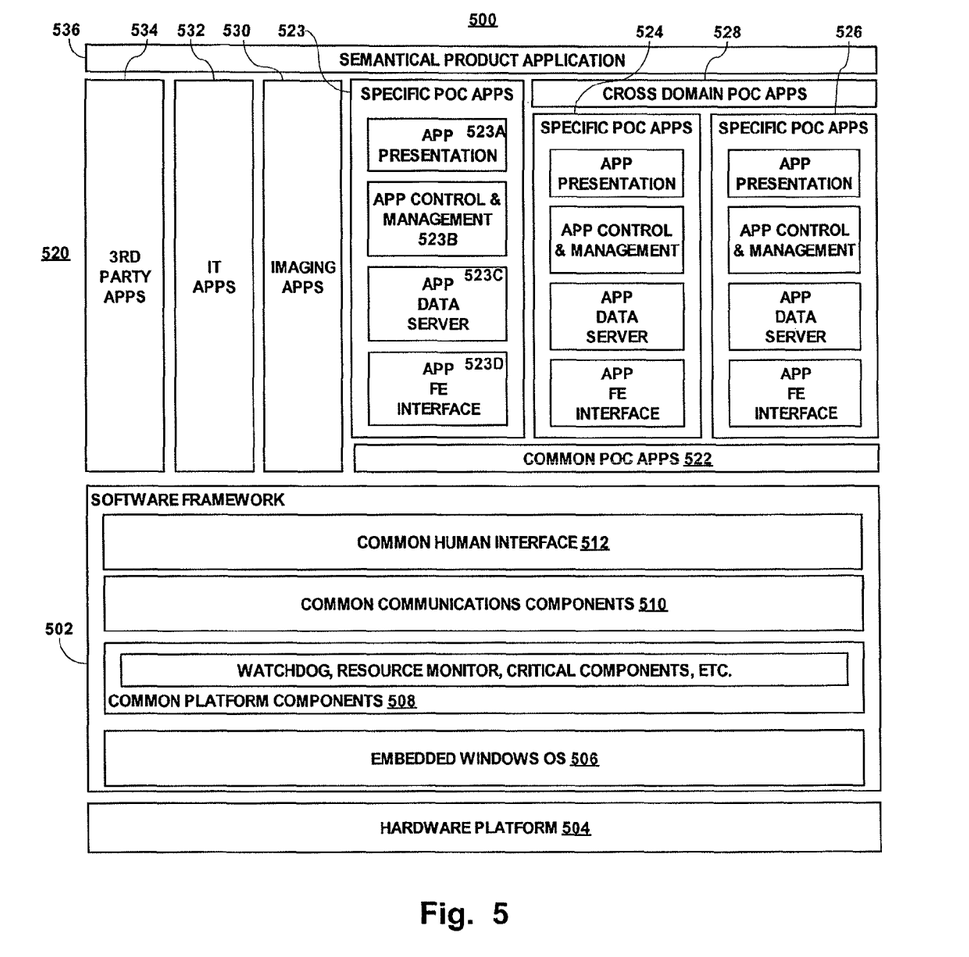
FIG. 5 is a diagram illustrating the relationship between different components of the software controlling the central unit.

FIG. 5 illustrates the relationship and interaction among different components of the central unit 300, including both the hardware platform 504 (as illustrated in FIG. 3 and FIG. 4) and a system executable application 500. As described above, an executable application is any set of executable instructions which may be used, e.g. to control the operation of a programmable processor. It may include software, firmware and hardware, as appropriate, and one skilled in the art will understand how to partition the executable application into software, firmware and hardware, and the design criteria and tradeoffs involved. Because, as described above, the components illustrated in FIG. 5 are implemented on a hardware system based on available PC systems, the executable application described in FIG. 5 is implemented in software, and will be termed system software 500 below.

Each element in FIG. 5 is represented by a rectangle. In general, elements, and the functions they provide, at lower levels of FIG. 5 may be accessed by elements at higher levels. At the bottom of FIG. 5 is the hardware platform 504. The hardware platform 504 provides the hardware functions, described in more detail above, such as: providing control signals to, and receiving status and patient physiological parameter information from, patient monitoring and/or treatment devices 210, 212, 214, 250, 260; exchanging data over the critical care area LAN 205 and hospital LAN 230; providing image representative signals to display devices 222, 225, 321, 331 (FIG. 3), exchanging signals with panel I/O devices 410 (FIG. 4), and so forth. The hardware platform 504 is not part of the system software 500 illustrated by the remainder of FIG. 5.

The system software 500 illustrated in FIG. 5 includes a software framework 502 providing particular functions. The software framework 502 provides the software infrastructure for support of point of care based medical modules, such as the modules 210, 212, 214, 250, 260 (FIG. 2, FIG. 3, FIG. 4). As used herein, the point of care (POC) is the area, in the vicinity of the patient, in which medical treatment is provided to a patient. The software illustrated in FIG. 5 may be embodied in PC based products. Table 1 (below), describes in detail the functions provided by the respective software components illustrated in FIG. 5.

The software framework 502 includes a hardware dependent operating system 506, which in FIG. 5 is an embedded windows operating system (OS) 506. For example, an embedded version of Windows XP (by Microsoft Corp) OS 506 may be included in the software framework 502. The OS 506 interacts with the hardware 504, which may be different from product to product, or may change or be updated over time. The OS 506 also provides a set of application program interfaces (APIs) which are sets of common software interfaces which may be used by the remainder of the software and which remain unchanged despite differences in the hardware 504. The remainder of the software illustrated in FIG. 5 is related to providing the functions required by the modules which may be controlled by the central unit 300.

The software framework 502 further includes a set of common platform components 508 (see Table 1 (below)). These components provide monitoring and executive functions for the central unit 300. Specifically, a watchdog function, a resource monitor, and a monitor for critical components are provided by the common platform components 508. In addition, the common platform components 508 provide security, lifetime management, diagnostics, real time infrastructure and event management, safety and availability management, and user set up configuration support for the central unit 300.

The software framework 502 also provides common communications component 510 (see Table 1 (below)). More specifically, the common communications component provides access to the PAN 216, the critical care area network 205 and any other networks to which the central unit 300 may be coupled, such as the hospital network 230 (FIG. 3). The common communications component 510 also provides peripheral support, e.g. communications with any other auxiliary device via the serial port, 416, the USB port 418, the expansion card port 422 and/or any other device which may be coupled to the central unit 300, for example, via boards mounted in the IDE bus 426 or PCI bus 428.

The software framework 502 also provides a common human interface component 512 (see Table 1 (below)). The common human interface component 512 provides functions for displaying graphical user interfaces (GUIs) on display devices 225, 321, 331 (FIG. 3, FIG. 4) and for coordinating the user inputs received from the input devices, such as keyboard 322 and mouse 324, with the displayed GUI. This enables a user to control the configuration and operation of the system and to receive status and data representing patient physiological parameters from the system. These functions also provide parameter signal group support, deployment support, and user help.

These functions also include those GUI functions which are specific to a patient monitoring and treatment module, for example, support for the display of waveforms, such as EKG waveforms or respirator loops, maintenance of trends, and generation of reports. These GUI functions also include the ability for a user to arrange on the screen of the display device the images representing the physiological parameters of the patient. That is, to be able to move those images around on the screen, to resize them, to remove an image displaying a physiological parameter and/or to insert an image displaying a different physiological parameter. The common human interface 512 further supports maintenance of patient data and status, and the database containing these and/or other data items. The common human interface 512 component further provides alarm support and processing, including providing functions for generating an audible and/or visible alarm at the central unit 300 (FIG. 3, FIG. 4), and for transmitting alarm information to other locations, via the PAN 216, the critical care area network 205 and/or the hospital network 230. The common human interface component 512 also provides more standard GUI support for other software applications (described in more detail below), which may not be related directly to medical support.

The remainder of the components in the system software are application programs 520. An application program is software which uses functions provided by the software framework 502, described above, to support clinical domains and/or to provide clinical functions at the point of care. As used herein, a clinical domain is an area of a patient monitoring and/or treatment process. For example, patient monitoring is a clinical domain; patient ventilation is another clinical domain; anesthesia and fluid administration are others, and so forth. The system software 500 includes several types of application programs 520.

The application programs 520 include a set of common point of care (POC) applications 522 (CPOC) which are common to the clinical domains (see Table 1 (below)). The functions provided by the CPOC 522 are application-related but generic and not specific to any particular domain. That is, the central processor 402 in the central unit 300 executes at least a portion of the common code in the CPOC application 522 to support the operation of two or more of the patient monitoring and/or treatment modules 210, 212, 214, 250, 260.

For example, the CPOC application 522 may provide a home screen from which other functions may be selected and configured. Functions for configuring and controlling the central unit 300 itself may be selected from the home screen, including: software option handling; application selection and configuration; remote control, both wired and wireless, from e.g. slave control units (FIG. 4: 330) or other central units via the critical care area network 205 and/or the hospital area network 230 (FIG. 2); battery management; and so forth. In addition, functions related to patients may be selected from the home screen, including patient category, configuration, context, setup and demographic entry, editing, and transfer. The CPOC application 522 may also provide functions related to monitoring and/or treating patients, including: real-time processing of measurements, waveform display; alarm behavior, display and control; measurement setup and priority, events, trends, strip recordings; loop display; flow meter display; alarm limits and history, and so forth.

One skilled in the art will recognize that point of care (POC) patient monitoring and/or treatment modules, e.g. 210, 212, 214, 250, 260 (FIG. 3 and FIG. 4), are typically associated with a specific clinical domain. That is, the monitoring module 210 is associated with the patient monitoring domain; the anesthesia module 214 is associated with the anesthesia domain, and so forth. Specific POC applications (SPOC), of which three 523, 524, 526 are shown to simplify the figure, respectively correspond to POC modules for specific domain areas. The respective SPOC applications 523, 524, 526 interact with associated ones of the modules 210, 212, 214, 250, 260. For example, in FIG. 5, SPOC 523 may be associated with one type of POC module, e.g. anesthesia module 214; SPOC 524 may be associated with a different type of POC module, e.g. fluid management module 212; and SPOC 526 may be associated with another POC module, e.g. patient monitoring module 210.

Typically, SPOC applications 523, 524, 526 have a presentation function e.g. 523A, a control and management function e.g. 523B, a data server function e.g. 523C, and a pluggable front-end (FE) module interface function e.g. 523D. As used herein, the term pluggable front end module refers to a medical monitoring and/or treatment module, such as modules 210, 212, 214, 250, 260 (FIG. 2, FIG. 3 and FIG. 4), which may be connected to and disconnected from the central unit 300 during operation. The FE module interface function e.g. 523D, bidirectionally communicates with patient monitoring and treatment modules 210, 212, 214, 250, 260. These communications include control and status information and physiological parameter representative data. The data server function e.g. 523C makes the control status and physiological data available to other applications. The presentation function e.g. 523A makes the control, status and physiological data available to be displayed on the display devices 225, 321, 331 (FIG. 3). The control and management function e.g. 523B controls the operation of the SPOC and the FE module.

More specifically, the SPOC application 526, which is associated with a patient monitoring module 210, provides the specific functions required to control and interact with the monitoring module 210. As described in more detail in Table 1 (below), the monitoring SPOC 526 provides module management, control and report functions, such as: monitor setup; export protocol management; nurse call; and setting display modes, including bedside and surgical display modes. The monitoring SPOC 526 also provides physiological parameter monitoring functions, such as: EEG, $SpO_2$, respiratory mechanics, invasive and non-invasive blood pressure, body temperature, transcutaneous blood gases, and so forth.

The SPOC application 523, which is associated with the anesthesia module 214, provides the specific functions required to interact with the anesthesia module 214. As described in more detail in Table 1 (below), the anesthesia SPOC 523 provides module management, control and report functions such as: warm up; carrier gas selection, and so forth. The anesthesia SPOC 523 also provides anesthesia control and monitoring functions, such as anesthetic gas control, including $N_2O$, Xenon, etc.; consumption monitoring, and anesthetic gases supply, and so forth.

The SPOC application 524, which is associated with the fluid management module 212, provides the specific functions required to interact with the fluid management module 212. As described in more detail in Table 1 (below), the fluid management SPOC 524 provides functions supporting different fluid managements modes, including: total controlled infusion (TCI), total intravenous anesthesia (TIVA), and patient controlled analgesia (PCA). As described above, other medical monitoring and/or treatment modules 210, 212, 214, 250, 260, corresponding to other medical domains, are associated with SPOC applications which control and manage them. Details for these SPOCs are described in detail in Table 1 (below).

The application programs 520 further include cross domain POC applications (CDPOC), one of which 528 is shown in FIG. 5 to simplify the figure. CDPOC applications provide advanced integrated clinical information. This information may be derived from cooperative operation of two or more selected SPOC applications 523, 524, 526 controlling associated medical monitoring and/or treatment modules 210, 212, 214, 250, 260 in respectively different clinical domains such as monitoring, ventilation, anesthesia and/or fluid management. CDPOC applications coordinate the operation of the selected medical monitoring and/or treatment modules 210, 212, 214, 250, 260, and integrate data received from them, as described in more detail below. One skilled in the art will understand that other CDPOC applications may be included in the application programs 520 which coordinate different SPOC applications; that more than two SPOC applications may be coordinated by a CDPOC application, and that an SPOC application may be associated with more than one CDPOC application.

Referring specifically to FIG. 5, the CDPOC application 528 coordinates the operation of the fluid management SPOC 524 and the monitoring SPOC 526. The fluid management SPOC 524 controls the operation of a fluid management treatment module 212 which may be administering a medication to affect a particular patient physiological parameter, such as blood pressure. The monitoring SPOC 526 controls the operation of the patient monitoring module 210 to monitor the patient blood pressure, among other things. The CDPOC application 528 monitors the patient blood pressure, as reported by the monitoring SPOC application 526 and controls the fluid management SPOC application 524 to continually adjust the administration of the blood pressure medication to maintain the patient blood pressure within limits specified by the physician.

The application programs 520 may further include imaging applications 530, as described in more detail in Table 1 (below). These applications condition the various display devices, 225, 321, 331 (FIG. 3) to display designated images in 2D and 3D modes. These imaging applications 530 further provide user control of panning and zooming, and for 3D images setting a point of view. The imaging applications 520 may also be used to produce: a virtual film sheet for e.g. x-rays, CAT scans, or any other group of related images; a patient scanner; a viewer for DICOM (Digital Imaging and Communications in Medicine) images retrieved via a query/retrieve operation, and so forth.

The application programs 520 may further include information technology (IT) applications 532, as described in more detail in Table 1 (below). Such applications may include e.g. a chart assistant program, a remote viewing program, and other programs for exchanging and analyzing information. Other third party applications 534 may also be included in the application programs 520. As used herein, third party applications 534 may provide clinical functions which may provide a benefit at the point of care, and may be developed outside and independently of the architecture developed for the central unit 300 to interact with the medical monitoring and/or treatment modules 210, 212, 214, 250, 260. For example, medical image and report distribution, appointment scheduling, client records management, copayment tracking and billing, medical charting, insurance submission and billing, scheduling, and so forth are functions which may be provided by third party application programs 534.

A Semantical Product Application (SPA) 536 provides coordination for the application programs 520 included in the system software. The SPA 536 covers the target domain or domains of the system, as configured with selected medical monitoring and/or treatment modules 210, 212, 214, 250, 260. The SPA 536 uses, deploys and combines other application programs 520. More specifically, the SPA 536 includes SPOC 523, 524, 526 configuration; CPOC 522 configuration; and CDPOC 528 configuration functions, and so forth. The SPA 536 also provides version management for the system.

The central units 300 in the respective critical areas and/or the hospital employ substantially the same type of CPU 402 and are implemented to support the operation of the different types of patient monitoring and/or treatment modules 210, 212, 214, 250, 260. In addition, the central processor 220 in the respective central units 300 in the critical care area and/or the hospital employ substantially the same system software 500, described above, supporting the operation of the patient monitoring and/or treatment modules 210, 212, 214, 250, 260.

The hardware and software architecture described above and illustrated in FIG. 2, FIG. 3, FIG. 4 and FIG. 5 allows implementers to develop different products which address a desired medical domain or domains. As used herein, a product addresses the desired domains using the hardware and software architecture to provide a well defined set of applications for the target domains. That is a fabricator may produce a monitoring product by including a monitoring SPOC (e.g. 526) and a patient monitoring module (e.g. 210). Alternatively, further capability may be included, such as including a ventilation SPOC (not shown) and a ventilation patient treatment module (also not shown), a fluid management SPOC (e.g. 524) and a fluid management patient treatment module (e.g. 212), and an anesthesia SPOC (e.g. 523) and an anesthesia patient treatment module (e.g. 214). A CDPOC (e.g. 528) application may be added to coordinate the operation of two or more SPOC applications.

More specifically, a fabricator may implement a product such as a transportable breathing support equipment system. Such a device is illustrated in FIG. 2 in room 208. This system includes a central unit 300 (FIG. 3) (not shown) which incorporates a central processor 208B and docking connectors 240. A ventilator module 208A is coupled to the central processor 208B and a display device 208C via a PAN 208D. The ventilator module 208A controls a ventilator device (not shown). The ventilator device regulates the flow of breathable gas from a source (not shown) to the lungs of the patient. The ventilator module 208A includes at least one battery 207 (see FIG. 2) which powers the module 208A and the ventilator device itself during transportation. The docking connectors 240 allow other modules, such as a patient monitoring module 210, an anesthesia module 214 and/or a fluid management module 212, to be connected to the breathing support equipment system if desired. The system software 500 (FIG. 5) detects the presence of these modules and automatically loads the SPOC applications required to control the newly added modules, 210, 212, 214, 250, 260. The transportable breathing support equipment system may comprise a manually pushed, or power driven cart or trolley conveying the equipment.

Other products such as an emergency room product as illustrated in room 206 (FIG. 2) and including a patient monitoring and ventilator module, or an ICU room product as illustrated in room 204 with a patient monitoring, ventilator and fluid management module, both with capabilities of adding further modules as required, may be implemented in a similar manner.

As described above, a CDPOC application 528 can advantageously coordinate the operation of two or more SPOC applications 523, 524, 526, which in turn control the operation of associated patient monitoring and/or treatment modules 210, 212, 214, 250, 260. This coordination enables the central processor 220 (FIG. 2) to support monitoring operation of a patient treatment module 212, 214, 250, 260 by (a) deriving data, based on combinations of parameters derived from the patient monitoring module 210 and a patient treatment modules 212, 214, 250, 260, for presentation to a user, and/or (b) prompting a user with suggested patient treatment module 212, 214, 250, 260 configuration settings.

The central processor 220 may also verify the safety of the treatment by receiving data from the patient monitoring and/or treatment modules 210, 212, 214, 250, 260 and using said received data to determine whether settings of the treatment delivery devices attached to the patient treatment modules 212, 214, 250, 260 are compatible with the desired treatment to be delivered to a patient. That is, the central processor 220 may verify the safety of a desired treatment by comparing patient physiological parameters received following initiation of delivery of a treatment, or following a change in the treatment induced by a corresponding change in the settings of a patient treatment module 212, 214, 250, 260, with predetermined physiological parameter value response ranges. In response to a determination that the settings of a patient treatment module 212, 214, 250, 260 are incompatible with a desired treatment the central processor 220 may (a) automatically alter the settings and/or (b) initiate generation of an alert message to a user warning of the incompatibility.

This coordination among different patient monitoring and/or treatment modules 210, 212, 214, 250, 260 allows patient medical tests to be performed, and physiological parameters to be determined, by such a system, without requiring the use of more expensive, or more invasive testing methods. A single configured system as illustrated in FIG. 4 and FIG. 5, for example, advantageously automatically performs multiple different tests as described as follows. The tests in some instances may involve manual interaction. One skilled in the art will understand which patient monitoring and/or treatment modules to include in the system, how to coordinate the operation of these modules, and how to analyze the data from those modules to perform the desired medical tests.

A general form of such patient medical tests involves providing a predetermined physiological stimulus to a patient, monitoring the patient physiological parameters after the stimulus, and verifying an acceptable response. For example, the physiological stimulus may be (a) a medication, (b) a gas administered to said patient, (c) an electrical stimulus, (d) a physical or mechanical stimulus, (e) an application of heat or cold, (f) an acoustic stimulus, (g) a light stimulus and/or (h) a radiation stimulus. The patient physiological parameters monitored may be (a) BP, (b) HR, (c) RR, (d) $SpO_2$, (e) $O_2$, (f) $CO_2$, (g) NBP, (h) EEG and/or (i) blood gas parameters.

In the system described above, the central processor 220 (FIG. 4) may initiate a stimulus by conditioning a patient treatment module 212, 250, 260 to temporarily change its operational setting, and using the patient monitoring module 210 to monitor subsequent physiological parameters to verify an acceptable response.

A more specific example of a medical test is a respiratory systolic variation test (RSVT), which may be performed by such a system. This test determines the blood filling conditions in the left atrium. It enables a physician to manage fluid input and output of a patient, and lung recruitment efforts (hypovolemea is often the reason for a patient not tolerating pressure-controlled inverse ratio ventilation (PCIRV)). The result of this test is a patient physiological parameter which may be displayed on the display devices 225, 321, 331 (FIG. 3). Use of the system described above to provide the RSVT test is more accurate and less invasive than the use of a single use PA catheter, which at the present time costs around $100.

A Gedeon non-invasive cardiac output test (NICO) may also be performed by the system described above. This test estimates output of the left ventricle and effective gas exchange area of the lungs (i.e. the effective lung volume (ELV). It enables a physician to titrate the positive end-expiratory pressure (PEEP) for optimal CO and ELV after initiating mechanical ventilation. As used herein, the term "titrate" refers to the adjustment of a patient treatment parameter (such as the PEEP pressure) such that a desired patient physiological parameter is achieved (that is, optimal CO and ELV). The titration may be performed manually by the physician in response to the results of the test, or may be performed automatically under the control of a CDPOC (not shown) programmed to perform the test and titrate the PEEP parameter. The results of this test may be displayed on the display devices 225, 321, 331 (FIG. 3). This test also aids a physician in starting or monitoring inotropic (i.e. cardiac output enhancing) drug therapy. Use of the system described above to perform the NICO test is less invasive than the conventional method and more accurate than other NICO methods.

A lung mechanics calculation test (LMC) may also be performed by the system described above. This test permits the modeling of a patient respiratory system in terms of elastic and resistive forces. More specifically, this test may determine inflection points in the respiratory cycle, i.e. points of alveolar collapse (atelectasis) during expiration and hyperinflation during inspiration. This test may also calculate physiological dead space, i.e. air which is inhaled by the body in breathing, but which does not partake in gas exchange. The results of the former test may be numerical or a graphic display, and the results of the latter test may be a numerical display, either or both of which may be displayed on the display devices 225, 321, 331 (FIG. 3). The physician may use the results of this test to titrate the settings after initiating mechanical ventilation, or a CDPOC may be programmed to titrate the settings automatically. The LMC test has been tested and widely published. It is considered state-of-the-art at this time for lung mechanics. The NICO test requirements, described above, may be combined with this test.

A stress index test (SI) may also be performed by the system described above. This test quantifies the stress on the lungs induced by mechanical ventilation. More specifically this test detects and measures the effect of cyclic stretch, i.e. recruitment of alveola at the extreme end of inspiration and collapse at the extreme end of expiration. The results of this test may be numeric or graphical and may be displayed on the display devices 225, 321, 331 (FIG. 3). A physician may use the results of this test to titrate ventilator settings, such as PEEP and tidal volume ($V_T$) to reduce stress on the lungs during ventilation, or a CDPOC may be programmed to titrate the settings automatically. The results of this test may also be used to predict the probability of success of a lung recruitment attempt. Ventilator settings made according to the SI test have been proven to reduce inflammatory markers in lung tissue.

An automatic lung parameter estimator test (ALPE) may also be performed by the system described above. This test assists a physician in quantifying the amount of pulmonary shunt and the distribution of pulmonary circulation (e.g. ventilation-perfusion ratio (V/Q) scatter). This test may also detect and quantify cardiac congestion, i.e. congestive heart failure (CHF). The results of this test may be numeric or graphical and may be displayed on the display devices 225, 321, 331 (FIG. 3). A physician may use the results of this test to determine the use of diuretics and inotropic drugs to manage CHF. This test provides a comprehensive model of hemodynamic status and blood gasses non-invasively. This may be useful to a physician in the detection and management of CHF, which is a widespread disease, especially prevalent among respiratory patients.

Diaphragm electromyographically (EMG) controlled ventilation may also be advantageously performed by the system described above. In this ventilation mode the electrical signal related to the diaphragm muscle contraction is detected using electrodes on an oesophageal catheter. Because contraction of the diaphragm muscles occurs when a patient begins to take a breath, the EMG signal may be used to trigger the ventilator to begin a respiration cycle. Thus, this ventilation mode permits the patient's brain to advantageously control respiratory support. This mode may be selected by a user selection via the interaction of the GUI and user input devices such as the keyboard 322 and mouse 324, or by panel I/O devices on the main control panel 320 and/or slave control panel 330 (FIG. 3, FIG. 4). Using EMG signals to trigger respiration permits ventilation to be more closely matched to the patient. This enables support of spontaneous breathing for a wider range of patients. This, in turn, makes mask ventilation more feasible, reducing complications associated with intubation, such as nosocomial pneumonia. These electrical signals may also provide ECG signals to measure the posterior of the heart and potentially detect atrial arrhythmias. The results of an ECG using EMG signals may be displayed on the display devices 225, 321, 331 in graphical form. An alarm may also be sent if an arrhythmia is detected. Detection of cardiac ischemia and atrial arrhythmias permits earlier intervention.

The system described above may also be used to perform electrical impedance tomography (EIT). EIT may provide continuous, breath-to-breath, and beat-to-beat anatomical images of respiratory and cardiac dynamics and distribution, respectively. More specifically, the physician may see and quantify areas of atelectasis and hyperinflation in the lungs and/or may see and quantify the output of the right ventricle and the deposition of blood in the lungs with each heartbeat. Electrodes for providing current and sensing voltage are applied to the patient and appropriate signals are applied to them to sense the conductivity of the respective portions of the body. From these readings, an anatomical image, or real-time series of images, may be synthesized. The display generator 222 (FIG. 4) generates signals representing these patient anatomical images. In order to maintain the display of these images in real time, the interface between the processor 402 and the display generator 222 provides substantially real time bidirectional communications. These images may be displayed on the display devices 321 and 331 on the main control panel 320 and slave control panel 330, respectively. These images may also be supplied to the larger display device 225 on the slave display panel 224. The physician may optimize ventilation parameters to address V/Q mismatch in which lung compartments are either ventilated but not perfused, or perfused but not ventilated. Early intervention, available from EIT images, may prevent cascade of lung injury leading to acute respiratory distress syndrome (ARDS) and sepsis. Use of EIT also has the possibility to reduce the number of CT and X-ray images required, and the intra-hospital transport required for them.

Referring again to FIG. 5, the embedded operating system 506 is configured to monitor the input/output ports, which may include the serial port, 416, the USB port 418, the expansion card port 422, the Ethernet ports 404, 406, and/or the panel I/O ports 410 to detect when a hardware device is newly connected to the system. When newly connected hardware is detected, at least the portion of the software required by the system software 500 to interact with this new hardware is retrieved from a mass memory, installed in the RAM 414 and made available to the operating system 506 and the rest of the system software 500. This operation is sometimes called "plug-and-play". The mass storage device may be local to the central unit 300, or may be remotely located (i.e. at a central location in the hospital) in which case it is retrieved via an Ethernet connection. When the SPOC application 523, 524, 526 is retrieved and loaded into RAM 414, the newly connected module 210, 212, 214, 250, 260 is coupled to it. The newly connected patient monitoring and/or treatment module 210, 212, 214, 250, 260 then is controlled by the central unit 300 and begins functioning.

As described above, a patient monitoring and/or treatment module 210, 212, 214, 250, 260 is sometimes removed from a central unit 300 in one location and reconnected to a central unit 300 at a different location (FIG. 3, FIG. 4). When, a patient monitoring and/or treatment module 210, 212, 214, 250, 260 is reconnected to a central unit 300, the operating system 506 advantageously detects its presence and identifies the SPOC 523, 524, 526 required to control it. If the required SPOC 523, 524, 526 is already loaded, then it is coupled to the newly connected module 210, 212, 214, 250, 260. If the required SPOC 523, 524, 526 is not already loaded, it is retrieved from a mass storage device, as described above.

A system described above integrates passive patient monitoring modules 210 (FIG. 3) and active treatment modules 212, 214, 250, 260 (infusion pumps, ventilators, anesthesiology equipment, incubators etc.) with a central unit 300 and associated system software 500 which receives physiological parameter data and operational status information from and supplies control information to both types of modules. The software 500 permits modules to be disconnected from, and reconnected to the central unit 300. The software 500 also permits interoperation of two or more of the modules cooperatively. The system reduces human error, improves speed of automatic adaptation of treatment, and of adapting treatment where human intervention is involved. In addition, the system improves the speed and accuracy of generating alerts, which may be crucial in a critical care unit such as an operating room. The system also saves space and cost, combines and groups alarms, provides consolidated documentation, facilitates module transportation and facilitates user operation. It reduces the problems presented to a healthcare worker in having to control multiple independent pieces of equipment. Because the modules may bidirectionally communicate with each other, tasks of supplying monitoring parameters to therapeutic modules, previously done manually, are advantageously accomplished automatically reducing human error. The critical care system may employ rules and programmed instruction governing addition of modules to the system. The integrated critical care system advantageously also provides a consistent user interface in both look and feel for the patient monitoring and therapeutic and life sustaining modules. This facilitates user friendly operation and reduces training required to educate a healthcare worker to operate the system compared to individual modules.

TABLE 1

| SW Component | Functions |
|---|---|
| SW Framework | Waveform support |
| | Parameters Signal Group Support |
| | Alarm Support |
| | Event Support |
| | Reporting Support |
| | Trend Support |
| | GUI Components |
| | Deployment Support |
| | Diagnostics |
| | Peripheral Support |
| | Help |
| | Screen Layout Support |
| | Safety and Availability |
| | Hospital Network and Interface and Support |
| | Critical Care Network Interface and Support |
| | Patient Area Network Support |
| | Security |
| | User/Setups Configuration Support |
| | Patient Data/State Support |
| | Lifetime Management |
| | Database |
| | Real-time Infrastructure |
| | Communication Mechanisms |
| | IT and Third Party App Support |
| | Etc |
| CPOC | Real-time Waveforms |
| | Real-time Measurements |
| | Real-time Alarm Behavior, Display and Control |
| | Home-screen |
| | Alarm Limits |
| | Trends |
| | Events |
| | Alarm History |
| | Remote/Bed to Bed View |
| | Calculations |
| | Strip Recordings |
| | Real-time Loops |
| | Real-time Flow Meters |
| | Demographics |
| | Patient Transfer |
| | Network Transfer |
| | Remote Control |
| | Monitor/Patient State Handling |
| | SW Option Handling |
| | Patient Context |
| | User Context |
| | Vital View |
| | Module/Patient Configuration/Setups |
| | Patient Category |
| | Full Disclosure |
| | Application Selection and Configuration Tools |
| | Flight Recorder |
| | Wireless Control |
| | Remote Keypad Handling |
| | Battery Management |
| | Measurement Setup and Priority |
| | Message Management |
| | Print Screen |
| | Taskcards |
| | Localization |
| | Etc |
| Ventilation Management and Gas Monitoring SPOC | PO1 |
| | IntrPEEP |
| | Sigh |
| | Suction |
| | Nebulize |
| | IMV (as example for a breathing mode) |
| | Recruitment |
| | Lung functions |
| | Smart Care |
| | NIV |
| | Monitor Respiratory System |
| | Insp/Exsp Hold |
| | NIF |
| | RSB |
| | RC |
| | CO2 Monitoring (including VCO and VDS) |
| | Leakage Compensation |
| | Nurse Call |
| | ILV |
| | HF |
| | Airway Temperature |
| | Flow and airway pressure monitoring |
| | Oxygen |
| | Localization |
| | Etc |
| Monitor SPOC | ST Measuring Points |
| | OCRG |
| | EEG Power Spectra |
| | Cardiac Output |
| | Wedge |
| | Monitor Reports |
| | Respiratory Mechanics |
| | Surgical Display |
| | MIB Management |
| | ECG Control |
| | Invasive Pressure Control |
| | SPO2 Control |
| | Respiration Control |
| | Body Temperature Control |
| | NIBP Control |
| | EEG Control |
| | Transcutaneous Blood Gas Control |
| | End Tidal CO2 Control |
| | Arrhythmia Control |
| | ECG Lead Management |
| | Fractional Inspired O2 Control |
| | MultiGas Control |
| | Export Protocol Management |
| | OR Mode |
| | Monitor Setup |
| | Nurse Call |
| | Auto Dual View |
| | Auto Source Switching |
| | Localization |
| | Etc |
| Anesthesia Gas Mixing SPOC | Air, oxygen, and N2O control |
| | Carrier gas selection |
| | ORC |
| | (Xenon) |
| | Fresh gas flow |
| | Low and minimal flow |
| | Monitors gas supply |
| | Consumption monitoring incl. Prices |
| | Agas control |
| | Warm-up |
| | Agas monitoring |
| | Plug and play of a-gases |
| | Inspiratory control |
| | Expiratory control |
| | MAK monitor |
| | Quantitative anesthesia |
| | Localization |
| | Etc |
| Fluid SPOC | TCI |
| | TIVA |
| | PCA |
| | Localization |
| | Etc |
| CDPOC's | Anesthesia |
| | No agas without gas flow |
| | Acone |
| | Open Lung Tool |

TABLE 1-continued

| SW Component | Functions |
|---|---|
| | Electrical Impedance Tomography (EIT) |
| | Respiratory Systolic Variation Test (RSVT) |
| | NICO |
| | Lung Mechanics Calculation (LMC) |
| | Automatic Lung Parameter Estimator (ALPE) |
| | Advanced Cardiopulmonary Integration Screens |
| | BiPAP |
| | SMART Alarms |
| | SmartCare |
| | Localization |
| | Etc |
| Other Applications | IT |
| | ChartAssist |
| | Remote View |
| | MegaCare |
| | BU-IT |
| | Localization |
| | Etc |
| | Imaging |
| | 2D |
| | 3D |
| | Virtual Film Sheet |
| | Patient Browser |
| | Dicom Query/Retrieve |
| | Localization |
| | Etc |
| | Third Party |
| | MagicWeb |
| | Cypress |
| | Localization |
| | Etc. |

What is claimed is:

1. A transportable breathing support equipment system, comprising:
    a device for providing a flow of breathable gas;
    a ventilator operatively coupled to the device and using said flow of breathable gas to support patient breathing during transportation;
    at least one battery for supplying power to said device and said ventilator during transportation; and
    a central unit comprising a plurality of docking connectors for connecting the central unit with the ventilator and for connecting the central unit with at least one of a plurality of different modules selected from a group consisting of:
    a patient monitoring module for acquiring and processing signals derived from sensors suitable for attachment to a patient,
    a module supporting delivery of anesthesia to a patient, and
    a module supporting infusion pump control;
    wherein the at least one of a plurality of different modules are interchangeably connectable between the plurality of docking connectors.

2. The transportable breathing support equipment system of claim 1, further comprising:
    a central processor in the central unit; and
    a ventilator module for controlling the ventilator,
    wherein the ventilator module is coupled to the central processor.

3. The transportable breathing support equipment system of claim 2, wherein the ventilator module is coupled to the central processor by a network.

4. The transportable breathing support equipment system of claim 2, wherein the central processor is connected to the at least one of a plurality of different modules by a network.

5. The transportable breathing support equipment system of claim 2, further comprising: a display device coupled to the central processor.

6. The transportable breathing support equipment system of claim 5, wherein the display device displays data received from the at least one of a plurality of different modules.

7. The transportable breathing support equipment system of claim 6, wherein the data received from the at least one of a plurality of different modules includes at least one of, settings of the at least one of a plurality of different modules, data representative of a respiration loop, and data representative of a fluid drip rate.

8. A transportable breathing support equipment system, comprising:
    a ventilator device configured to regulate a flow of breathable gas from a source of breathable gas to a patient;
    a ventilator module operably coupled with the ventilator device, the ventilator module being configured to control operation of the ventilator device;
    at least one battery configured to supply power to said ventilator device and to said ventilator module during transportation; and
    a central unit comprising a plurality of docking connectors for connecting the central unit with the ventilator module and for connecting the central unit with at least one of a plurality of different modules selected from a group consisting of:
    a patient monitoring module for acquiring and processing signals derived from sensors suitable for attachment to a patient,
    a module supporting delivery of anesthesia to a patient, and
    a module supporting infusion pump control;
    wherein the at least one of a plurality of different modules are interchangeably connectable between the plurality of docking connectors.

9. The transportable breathing support equipment system of claim 8, further comprising a central processor in the central unit, said ventilator module being coupled to the central processor.

10. The transportable breathing support equipment system of claim 9, wherein the ventilator module is coupled to the central processor by a network.

11. The transportable breathing support equipment system of claim 9, wherein the central processor is connected to the at least one of a plurality of different modules by a network.

12. The transportable breathing support equipment system of claim 9, further comprising a display device coupled to the central processor.

13. The transportable breathing support equipment system of claim 12, wherein the display device displays data received from the at least one of a plurality of different modules.

14. The transportable breathing support equipment system of claim 13, wherein the data received from the at least one of a plurality of different modules includes at least one of, settings of the at least one of a plurality of different modules, data representative of a respiration loop, and data representative of a fluid drip rate.

* * * * *